(12) United States Patent
Lee et al.

(10) Patent No.: US 9,390,825 B2
(45) Date of Patent: Jul. 12, 2016

(54) X-RAY DISTRIBUTION ADJUSTING FILTER, CT APPARATUS AND METHOD THEREOF

(71) Applicant: Electronics and Telecommunications Research Institute, Daejeon-si (KR)

(72) Inventors: Soo-Yeul Lee, Daejeon si (KR); In-Bum Lee, Daejeon-si (KR); Jeong-Won Lee, Daejeon-si (KR); Yoon-Seon Song, Daejeon-si (KR); Hyung-Wook Noh, Daejeon-si (KR)

(73) Assignee: ELECTRONICS AND TELECOMMUNICATIONS RESEARCH INSTITUTE, Daejeon-Si (KR)

( * ) Notice: Subject to any disclaimer, the term of this patent is extended or adjusted under 35 U.S.C. 154(b) by 84 days.

(21) Appl. No.: 14/224,484

(22) Filed: Mar. 25, 2014

(65) Prior Publication Data

US 2014/0362971 A1 Dec. 11, 2014

(30) Foreign Application Priority Data

Jun. 5, 2013 (KR) .................. 10-2013-0064935

(51) Int. Cl.
*A61B 6/03* (2006.01)
*G21K 1/10* (2006.01)
*A61B 6/00* (2006.01)

(52) U.S. Cl.
CPC . *G21K 1/10* (2013.01); *A61B 6/032* (2013.01); *A61B 6/4035* (2013.01); *A61B 6/542* (2013.01)

(58) Field of Classification Search
CPC ..... G21K 1/10; G21K 1/04; G21K 2207/005; G21K 2201/067; A61B 6/4035
See application file for complete search history.

(56) References Cited

U.S. PATENT DOCUMENTS

| | | | |
|---|---|---|---|
| 4,873,707 A * | 10/1989 | Robertson | 378/18 |
| 7,082,189 B2 | 7/2006 | Yahata et al. | |
| 7,308,073 B2 * | 12/2007 | Tkaczyk et al. | 378/16 |
| 2007/0116181 A1* | 5/2007 | Arenson et al. | 378/156 |
| 2014/0294139 A1* | 10/2014 | Funk | 378/16 |

FOREIGN PATENT DOCUMENTS

DE 102011004737 A1 * 2/2011

* cited by examiner

*Primary Examiner* — Hoon Song
(74) *Attorney, Agent, or Firm* — Kile Park Reed & Houtteman PLLC

(57) ABSTRACT

An X-ray distribution adjusting filter, and a CT apparatus and method thereof are provided, in which the X-ray distribution adjusting filter has a hollow inner part, and when rotating, a shape thereof is changed according to rotation angles, such that intensity distribution of X-rays radiating toward a subject may be adjusted.

19 Claims, 10 Drawing Sheets

X-RAY DISTRIBUTION ADJUSTING FILTER, CT APPARATUS AND METHOD THEREOF

CROSS-REFERENCE TO RELATED APPLICATION(S)

This application claims priority from Korean Patent Application No. 10-2013-0064935, filed on Jun. 5, 2013, in the Korean Intellectual Property Office, the entire disclosure of which is incorporated herein by reference for all purposes.

BACKGROUND

1. Field

The following description relates to a technology of sensing bio-signal information and signal processing by radiating X-rays to a subject to obtain an internal image thereof.

2. Description of the Related Art

Since its discovery by Roentgen in 1895, X-rays have been a useful tool for looking into internal organs of the human body without dissection. Such X-rays have been widely used in many fields, such as orthopedics and cardiothoracic surgery, and the development of a computed tomography (CT) in the early 1970s ushered in a new era of three-dimensional images of internal organs of the human body obtained by tomography imaging.

An X-ray imaging method basically uses a mechanism in which x-rays are absorbed into the tissues of the human body. Depending on thickness of body tissues, and difference in X-ray absorption by tissues, signal strength received on a two-dimensional sensor (X-ray film or digital sensor) is different at every location, and such difference is expressed in gray levels of images.

When X-rays are absorbed into the human body, atoms are temporarily ionized, as a result of which body tissues or DNA binding may be damaged. Therefore, when the human body is exposed to intense, or a huge amount of X-rays, side effects including organ damage may occur. Accordingly, the department of radiology limits an X-ray dose exposed to the human body, and recommends a minimum use thereof.

In X-ray imaging of hands or feet, which are thin body parts, a small dose of X-rays is used. However, for thick body parts, such as pelvis or chest, a large dose of X-rays is required so that sufficient X-ray signals are sensed on a sensor side to get high quality X-ray images. However, an X-ray dose of CT imaging is in principle hundreds of times higher than that of a simple X-ray imaging, since CT imaging is conducted in such a manner that hundreds of X-ray images are captured while rotating 180 to 360 degrees around the human body to be reconstructed afterwards as tomographic images of internal human body. For this reason, even with a one-time CT imaging in the early 2000s, a person was exposed to an X-ray dose nearly equivalent to an amount a normal person is allowed to be exposed to in one year. Therefore, CT manufacturers have competed and made every effort to reduce an x-ray dose, and equipment is recently being released that reduce x-ray dose to a tenth of the existing equipment, with almost no image degradation.

The effort to reduce x-ray dose in CT imaging should be approached by considering the aspects of an X-ray source, a detector, and an algorithm for image reconstruction.

In an aspect of X-ray source, a method for emitting X-rays with a narrow energy band is being developed. X-rays are generated in such a manner that electrons are accelerated to collide with a metal, which generates a very large range of X-ray spectrum, thereby resulting in unnecessary exposure to radiation and degradation in image quality. Research has recently been conducted to develop good quality monochromatic x-rays by using carbon nanotubes, ultra-high energy laser, and the like.

In an aspect of detector, there has been research in improving sensitivity and a signal-to-noise ratio (SNR), and more recently, research has been actively conducted in developing a method for detecting single photon, leading to an expectation that detector performance may be enhanced to a higher level in the near future.

In an aspect of reconstruction, research has been conducted in developing a method for reducing noise of reconstructed CT images in a case where low X-ray dose or a small number of X-ray images are used. A method of repetitive reconstruction is mostly used to improve quality of CT images, but it presents the problem of taking a long time for reconstruction. However, a rapid development in GPU board as well as development in parallel processing allows repetitive reconstruction processing, even for a personal computer, within a few minutes.

SUMMARY

According to an exemplary embodiment, there is provided an X-ray distribution adjusting filter, and a CT apparatus, and a method thereof, in which an X-ray dose may be reduced, and images with optimal quality may be obtained.

According to an exemplary embodiment, an X-ray distribution adjusting filter includes a hollow inner part, in which the inner part has a long axis and a short axis, and when the X-ray distribution adjusting filter rotates, positions of the long axis and the short axis of the inner part are changed according to rotation angles toward a subject, such that X-ray intensity distribution is adaptively adjusted to an environment where a thickness and width of the subject are different.

When an X-ray source and an X-ray detector facing each other with the subject interposed therebetween revolve around the subject, the X-ray distribution adjusting filter rotates with an angle identical to an angle of the revolution of the X-ray source and the X-ray detector, such that the positions of the long axis and the short axis of the inner part toward the subject may be changed. In this case, when the X-ray source revolves to be disposed at a position to radiate X-rays in a lateral direction of the subject, the long axis of the inner part of the X-ray distribution adjusting filter may rotate to be directed toward the lateral direction of the subject, and when the X-ray source revolves to be disposed at a position to radiate X-rays in an anteroposterior direction of the subject, the short axis of the inner part of the X-ray distribution adjusting filter may rotate to be directed toward the anteroposterior direction of the subject.

The outer part of the X-ray distribution adjusting filter may have a cylindrical shape, and the inner part of the X-ray distribution adjusting filter may have a cylindroid shape. Alternatively, both of the outer part and the inner part of the X-ray distribution adjusting filter may have a cylindroid shape, in which each cylindroid of the outer part and the inner part may have a different long axis/short axis ratio. The X-ray distribution adjusting filter may have a frusto-conical shape. The X-ray distribution adjusting filter may have an array structure, in which a plurality of filters of different sizes are connected to each other or may be integrally formed.

According to another exemplary embodiment, there is provided a CT apparatus, which includes: a gantry configured to comprise an X-ray source and an X-ray detector, which are disposed to face each other with a subject positioned therebetween, and to revolve around the subject to scan the subject; an X-ray distribution adjusting filter, which is disposed between the X-ray source and the X-ray detector of the gantry, has a hollow inner part, and is configured to rotate according to revolution of the X-ray source and the X-ray detector such that a shape of the X-ray distribution adjusting filter is changed according to revolution angles to adjust intensity distribution of X-rays radiating toward the subject; and an actuator configured to rotate the X-ray distribution adjusting filter.

When the X-ray source and the X-ray detector revolve around the subject, the X-ray distribution adjusting filter rotates with an angle identical to an angle of the revolution of the X-ray source and the X-ray detector, and positions of a long axis and a short axis of an inner part of the X-ray distribution adjusting filter are changed, such that the X-ray distribution adjusting filter may adaptively adjust X-ray intensity distribution to an environment where a thickness and width of the subject are different.

The actuator may rotate the X-ray distribution adjusting filter so that when the X-ray source revolves to be disposed at a position to radiate X-rays in a lateral direction of the subject, the long axis of the inner part of the X-ray distribution adjusting filter is directed toward the lateral direction of the subject, and when the X-ray source revolves to be disposed at a position to radiate X-rays in an anteroposterior direction of the subject, the short axis of the inner part of the x-ray distribution adjusting filter is directed to the anteroposterior direction of the subject.

The outer part of the X-ray distribution adjusting filter may have a cylindrical shape, and the inner part of the X-ray distribution adjusting filter may have a cylindroid shape. Alternatively, both the outer part and the inner part of the X-ray distribution adjusting filter may have a cylindroid shape.

The CT apparatus may further include a controller configured to use physique information of the subject to select a filter corresponding to the subject's physique, or to adjust a position and distance of the filter. The controller adjusts, according to the X-ray source, a distance between the X-ray distribution adjusting filter and the X-ray source through the actuator according to physique or body tissues of the subject. The X-ray distribution adjusting filter may have a frusto-conical shape, and the controller may move the X-ray distribution adjusting filter of a frusto-conical shape through the actuator according to physique or body tissues of the subject.

According to still another exemplary embodiment, there is provided a CT method, which includes: along with revolution of an X-ray source and an X-ray detector, which are disposed to face each other in a gantry with a subject interposed therebetween, rotating an X-ray distribution adjusting filter, which has a hollow inner part and is disposed between the X-ray source and the X-ray detector; adjusting intensity distribution of X-rays radiating toward a subject by the X-ray distribution adjusting filter, of which shape is changed during rotation; obtaining projected data from the subject according to the adjustment of X-ray intensity distribution; and reconstructing the obtained projected data to obtain images.

The adjusting of intensity distribution of X-rays may include: when the X-ray source revolves to be disposed at a position to radiate X-rays in a lateral direction of the subject, controlling the actuator to rotate the X-ray distribution adjusting so that a long axis of the inner part of the X-ray distribution adjusting filter is directed toward the lateral direction of the subject; and when the x-ray source revolves to be disposed at a position to radiate X-rays in an anteroposterior direction of the subject, controlling the actuator to rotate the X-ray distribution adjusting filter so that a short axis of the inner part of the X-ray distribution adjusting filter is directed toward the anteroposterior direction of the subject.

The CT method may further include: receiving physique information of a subject to be imaged by CT; and selecting an X-ray distribution adjusting filter suitable for the received physique information of the subject among X-ray distribution adjusting filters of different sizes.

The CT method may further include: receiving physique information of a subject to be imaged by CT; and adjusting, according to the X-ray source, a distance between the X-ray distribution adjusting filter and the X-ray source according to the received physique information of the subject.

Figure 1:
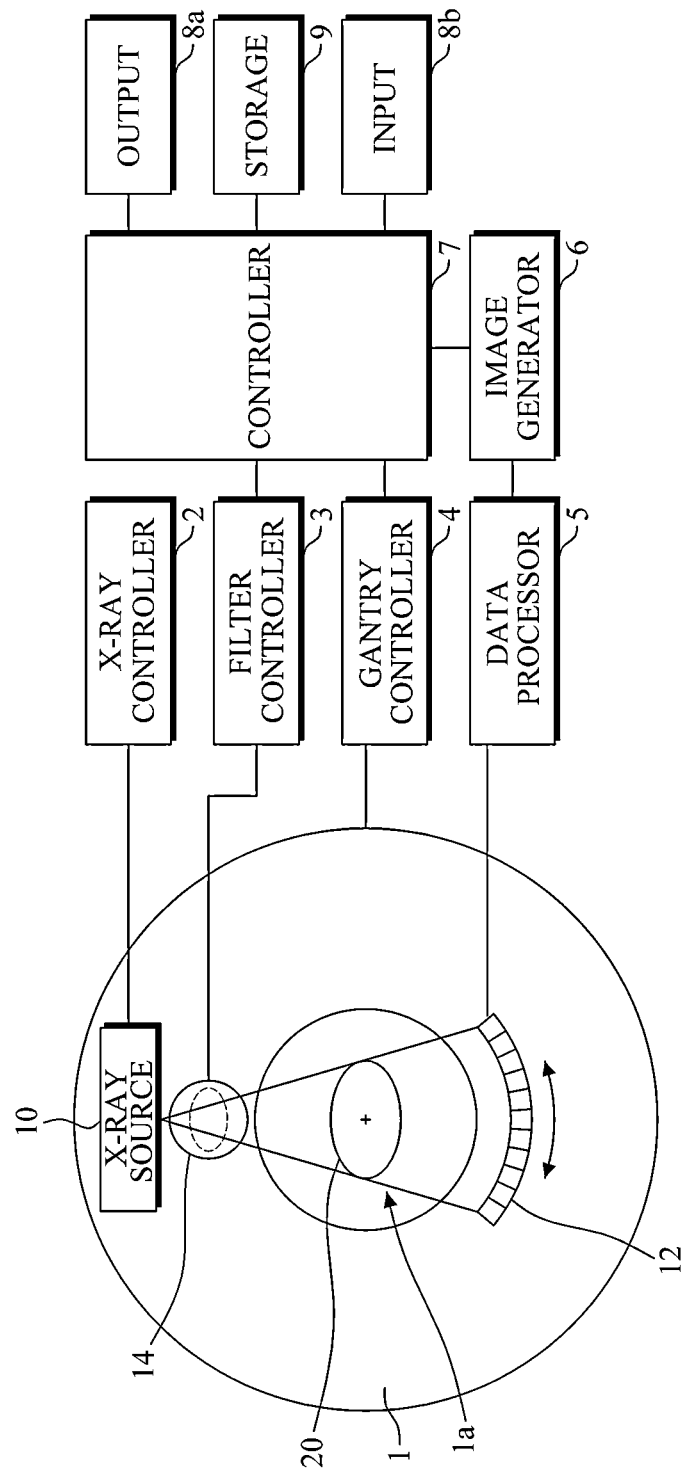
FIG. 1 is a view illustrating an example of a CT apparatus according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Hereinafter, an X-ray distribution adjusting filter, CT apparatus, and method thereof will be described in detail with reference to the accompanying drawings.

FIG. 1 is a view illustrating an example of a CT apparatus according to an exemplary embodiment.

The CT apparatus is an apparatus for identifying organ or skeletal abnormalities of a human body through Computed Tomography (CT) imaging of the human body 20, in which detected images may be three-dimensional. For convenient explanation, an object to be imaged is limited to the human body 20 in an exemplary embodiment, but may also be extended to all subjects, such as objects or animals, which may be imaged by CT, other than the human body 20.

A gantry 1 is a tunnel-shaped sphere, and the human body 20 passes through an opening 1a of the gantry 1. The gantry 1 includes an X-ray source 10 (hereinafter referred to as "source") that radiates X-rays to the human body 20 passing through the opening 1a, an x-ray detector 12 (hereinafter referred to as "detector"), and an X-ray distribution adjusting filter 14 (hereinafter referred to as "detector"). As illustrated in FIG. 1, the source 10 and the detector 12 are disposed to face each other, and the filter is positioned therebetween. According to an exemplary embodiment, the source 10, the detector 12, and the filter 14 are included in the gantry 1, and revolve along with revolution of the gantry 1.

The filter 14 adjusts intensity distribution of X-rays radiated to the human body 20 by the source 10. According to an exemplary embodiment, the filter 14 allows a minimum dose of X-rays to be radiated in the human body 20, and a dynamic range of the detector 12 to be used efficiently. Various structures and operations of the filter 14 will be described in detail with reference to the drawings described below.

According to an exemplary embodiment, in order to obtain 3-dimensional images using X-rays, the gantry 1, which includes the source 1, the detector 12, and the filter 14, is revolved. The gantry 1 is revolved by a gantry controller 4, which controls a revolution speed and a position of the gantry 1. An X-ray controller 2 provides power and a timing signal to the source 10. A filter controller 3 controls rotation of the filter, in which the filter controller 3 applies a driving signal to an actuator of the filter 14 so that when the source 10 and the detector 12 facing each other revolve, the filter 14 rotates with an angle identical to the revolution angle of the source 10 and the detector 12.

A data processor 5 performs sampling of analog data obtained from the detector 12, and to convert the data into a digital signal. An image generator 6 is configured to receive X-ray data sampled and digitized by the data processor 5 to restore X-ray projected images. A controller 7 applies a control signal to the X-ray controller 2, the filter controller 3, the gantry controller 4, and the data processor 5, to display images restored by the image generator 6 on a screen through an output 8a, and to store restored images in a storage 9. An input 8b receives physique information of a patient from a user.

Figure 2:
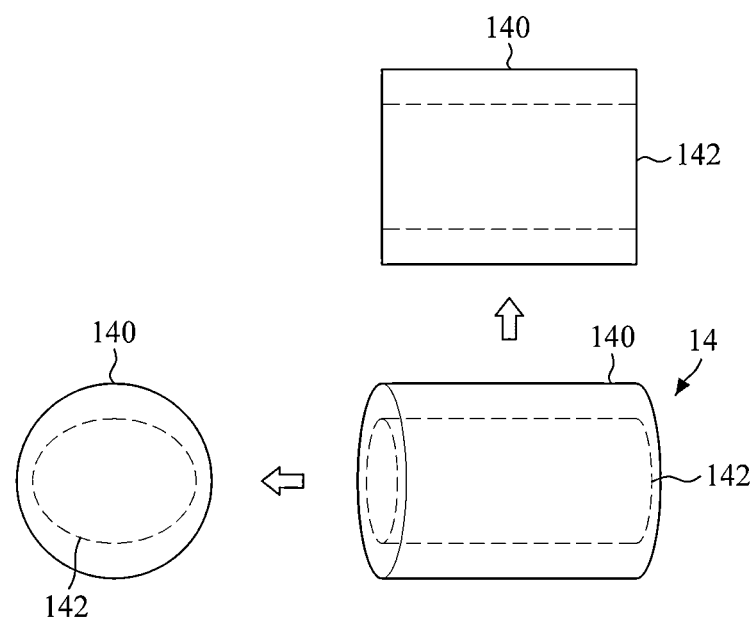
FIG. 2 is a view illustrating an example of an exterior appearance, a lateral surface, and a perspective view of a filter according to an exemplary embodiment.

FIG. 2 is a view illustrating an example of an outer shape, a lateral surface, and a perspective view of a filter 14 according to an exemplary embodiment.

Referring to FIG. 2, an outer part 140 and an inner part 142 of a filter 14 are integrally formed. The outer part 140 forms an exterior of the filter 14, and the inner part 142 is hollow. A shape of the filter 14 including the outer part 140 and the inner part 142 is changed by revolution, so as to provide the detector 12 with different X-ray beam profiles. An example of the filter 14, of which shape is changed by revolution, will be described below with reference to FIGS. 3 and 4.

According to an exemplary embodiment, the filter 14 has the outer part 140 of a cylindrical shape, and the inner part 142 of a cylindroid shape, as illustrated in FIG. 2. In another example, both the outer part 140 and the inner part 142 are of cylindroid shape, in which case, each cylindroid of the outer part 140 and the inner part 142 may have a different long axis/short axis ratio. A material of the filter 14 may be formed of aluminum, or a mixture of aluminum and other metal, but is not limited thereto, and other material may also be used.

Figure 3:
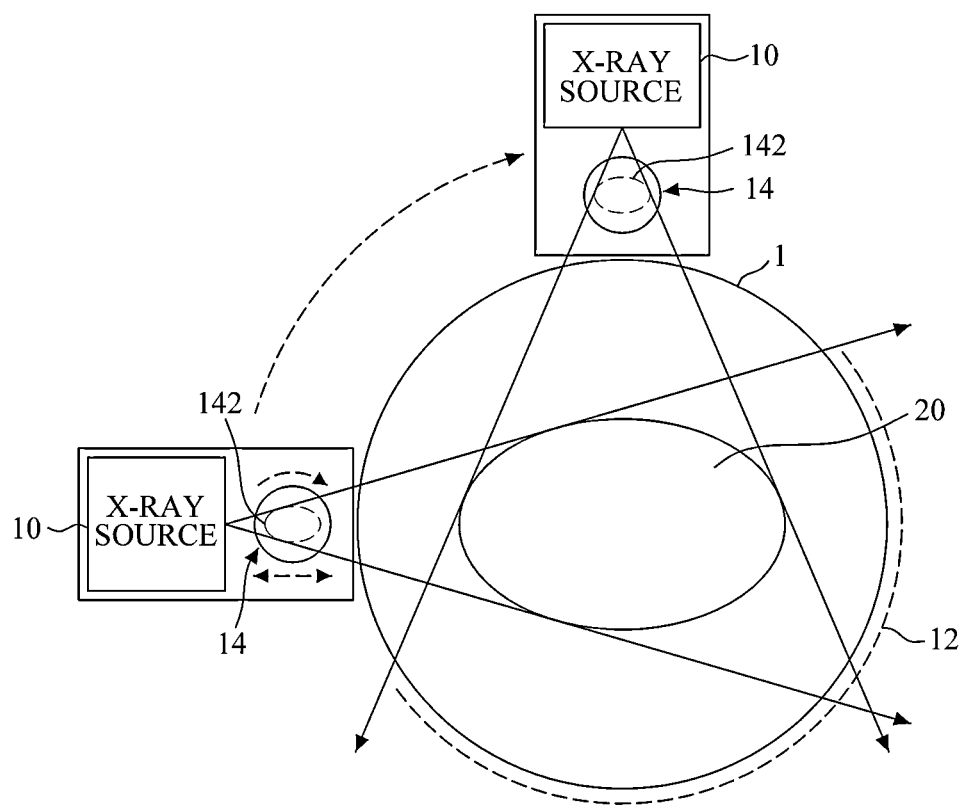
FIG. 3 is a view illustrating an example of a CT imaging concept using a filter according to an exemplary embodiment.

FIG. 3 is a view illustrating an example of a CT imaging concept using a filter according to an exemplary embodiment.

Referring to FIG. 3, in CT imaging, when a source 10 and a detector 12 facing each other revolve around a bore of the gantry 1, the filter 14 also rotates with an angle identical to the revolution of the source 10 and the detector 12. The filter 14 is rotated so that X-ray intensity distribution is adjusted adaptively to an environment where a thickness and width of the human body 20 irradiated with x-rays are different according to revolution angles.

For example, the filter 14 is rotated so as to change a position of a long axis and a short axis of the inner part 142 of the filter 14 directed toward the human body 20. Specifically, when the source 10 radiates X-rays in a lateral direction of the human body 20, the thickest part of the human body 20 is irradiated, but a part of the human body 20 to be irradiated rapidly becomes thinner toward the periphery, such that a long axis of the inner part 142 of the filter 14 is directed toward the lateral surface of the human body 20 (see a left filter in FIG. 3). By contrast, when the source 10 radiates X-rays in an anteroposterior direction of the human body 20, the thinnest, but wide part of the human body 20 is irradiated, such that a short axis of the inner part 142 of the filter 14 is directed toward the anteroposterior direction of the human body 20 (see an upper filter in FIG. 3).

According to an exemplary embodiment, each projected image obtained by revolution of the source 10 and the detector 12 is calibrated for every pixel by comparing with background images, which are projected images obtained in advance without the human body 20. After an appropriate filtering, the calibrated images are then back-projected to obtain cross-sectional CT images. Pixel values of the 3-dimensional cross-sectional images may be transformed into Hounsfield unit values that are in proportion to X-ray attenuation coefficient.

Figure 4:
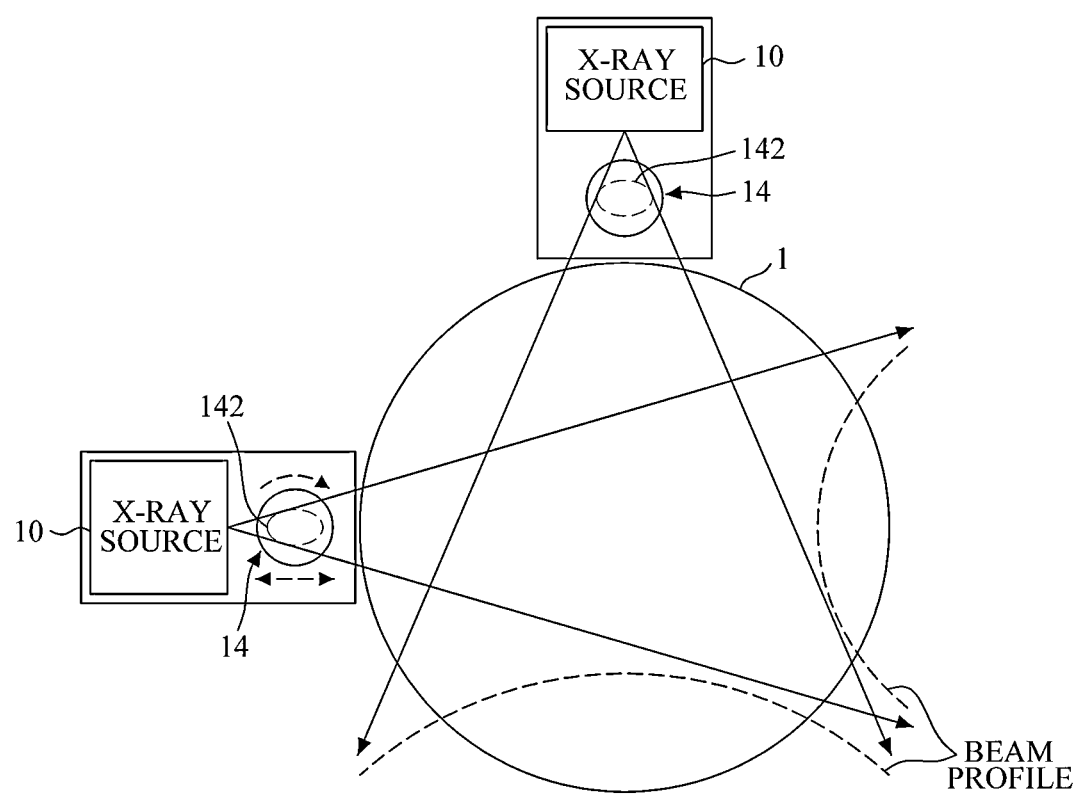
FIG. 4 is a view illustrating an example of an x-ray beam profile after passing through a filter according to an exemplary embodiment.

FIG. 4 is a view illustrating an example of an x-ray beam profile after passing through a filter according to an exemplary embodiment.

Referring to FIG. 4, widening and narrowing of the X-ray beam profile after passing through the filter 14 is repeated every 90 degree revolution according to revolution of the filter 14.

Generally, without such filter 14, intensity of an X-ray beam after penetrating through a human body would greatly increase as the beam moves away from the center of the body. For this reason, imaging the center and the periphery of the human body at the same time requires a detector to have a wide dynamic range, which causes difficulties in using detectors for medical imaging.

However, according to an exemplary embodiment, a thin part of the human body is prevented from being irradiated with unnecessarily large amounts of X-rays, and a height of the X-ray beam profile after passing through the human body is within a relatively narrow range, thereby enabling an effective use of a dynamic range of the detector 12.

According to an exemplary embodiment, physique of a patient is taken into consideration to radiate a minimum amount of X-rays. Hereinafter, various exemplary embodiments of filters considering physique of a patient will be described below with reference to FIGS. 5 to 9.

Figure 5:
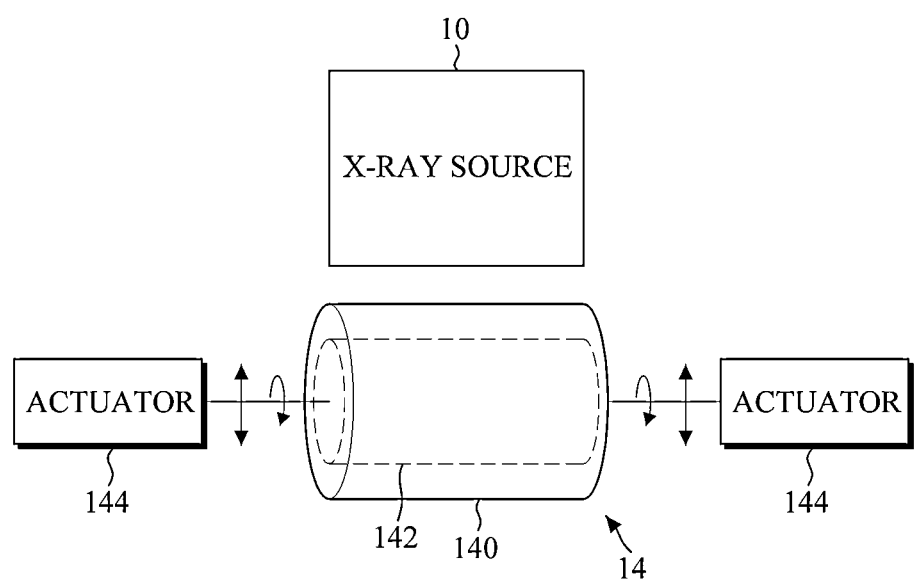
FIG. 5 is a view illustrating an example of adjusting a distance of a filter according to an exemplary embodiment.

FIG. 5 is a view illustrating an example of adjusting a distance of a filter according to an exemplary embodiment.

Referring to FIG. 5, an X-ray dose may be reduced according to physique of a patient, which becomes bigger or smaller as the filter 14 is moved toward or away from the source 10. For example, if physique of a patient is big, an actuator 144 moving the filter 14 is used to move the filter 14 toward the source 10. After moving closer to the source 10, the filter 14 is rotated at the same time as the source-detector revolution to obtain projected data through the detector, and as a result, images of a patient with a big physique may be effectively obtained by magnification effect. By contrast, if a patient has a small physique, the filter 14 is moved away from the source 10. After moving away from the source 10, the filter 14 is rotated at the same time as the source-detector revolution to obtain projected data through the detector, and as a result, images of a patient with a small physique may be effectively obtained by reduction effect.

Figure 6:
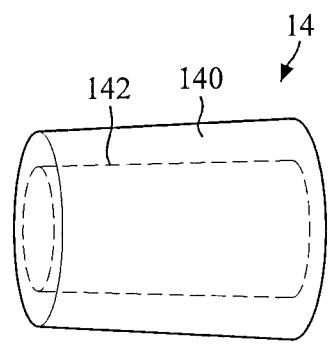
FIG. 6 is a view illustrating an example of a filter of a frusto-conical shape according to an exemplary embodiment.
Figure 7:
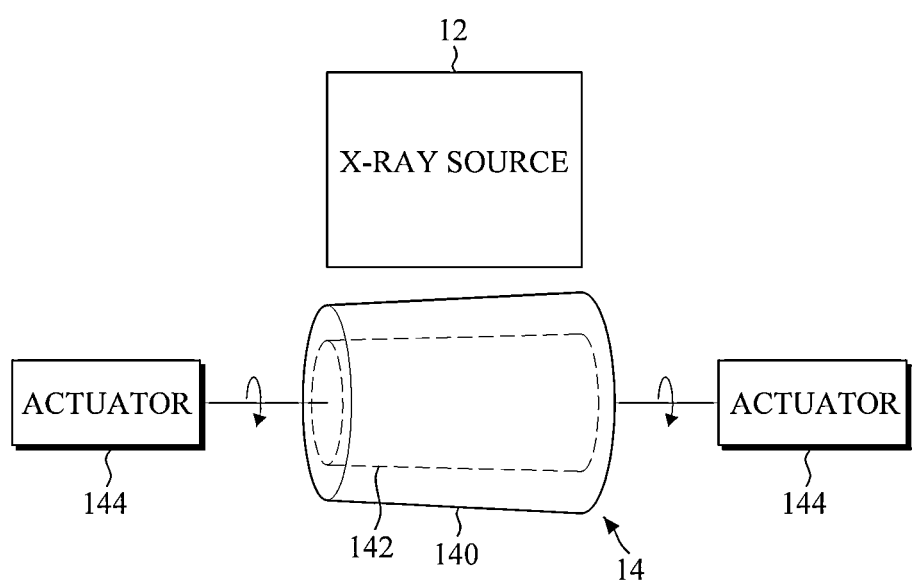
FIG. 7 is a view illustrating an example of operation of the filter in FIG. 6.

FIG. 6 is a view illustrating an example of a filter of a frusto-conical shape according to an exemplary embodiment, and FIG. 7 is a view illustrating an example of operation of the filter in FIG. 6.

Referring to FIGS. 6 and 7, the filter 14 is of a frusto-conical shape, of which size is reduced or increased along a horizontal direction of an axis. The actuator 144 moves the filter 14 of a frusto-conical shape in the horizontal direction of an axis according to physique of a subject. For example, for a patient with a big physique, the actuator 144 moves the filter 14 so that a large-diameter part of the filter 14 is irradiated with X-rays from the source 10. For a patient with a small physique, the actuator 144 moves the filter 14 so that a small-diameter part of the filter 14 is irradiated with X-rays from the source 10. After the filter 14 is moved appropriately in an axis direction according to physique of a patient, the filter 14 is rotated at the same time as revolution of the source and the detector to obtain projected data, and as a result, images of a patient, both big and small, may be simply imaged by using one filter 14.

In FIG. 7, the actuator 144 is disposed at both ends of the filter 14, but a position of the actuator 144 is not limited thereto. For example, the actuator 144 may be disposed at one end of the filter 14, and the other end of the filter 14 may be fixed.

Figure 8:
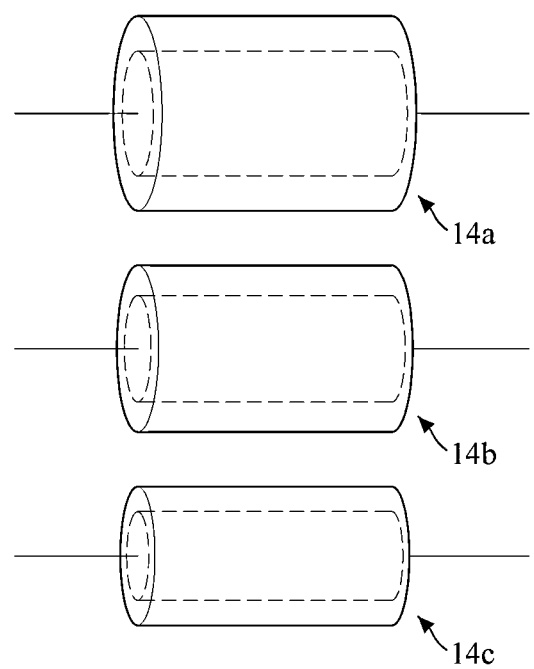
FIG. 8 is a view illustrating an example of filters of different sizes according to an exemplary embodiment.

FIG. 8 is a view illustrating an example of filters in different sizes according to an exemplary embodiment.

Referring to FIG. 8, filters 14a, 14b, 14c in sizes different from each other may be selected appropriately to be used according to a patient's physique. The filters may be selected or changed manually by a user, or by a simple operation of a mechanical apparatus.

Figure 9:
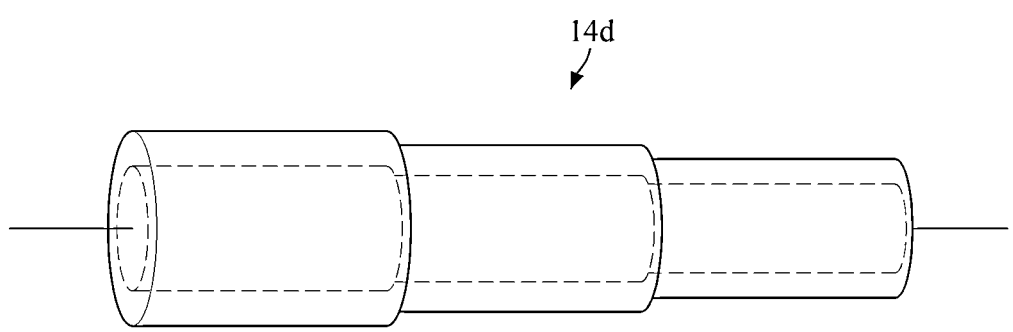
FIG. 9 is a view illustrating an example of a filter array including a plurality of filter units according to an exemplary embodiment.

FIG. 9 is a view illustrating an example of a filter array including a plurality of filter units according to an exemplary embodiment.

Referring to FIG. 9, after connecting filter units of different sizes along an axis, a filter array 14d may be used by being moved appropriately in the axis direction according to a patient's physique. The filter array 14d may be formed by connecting each of the filter units, or by integrally forming the filter units.

Figure 10:
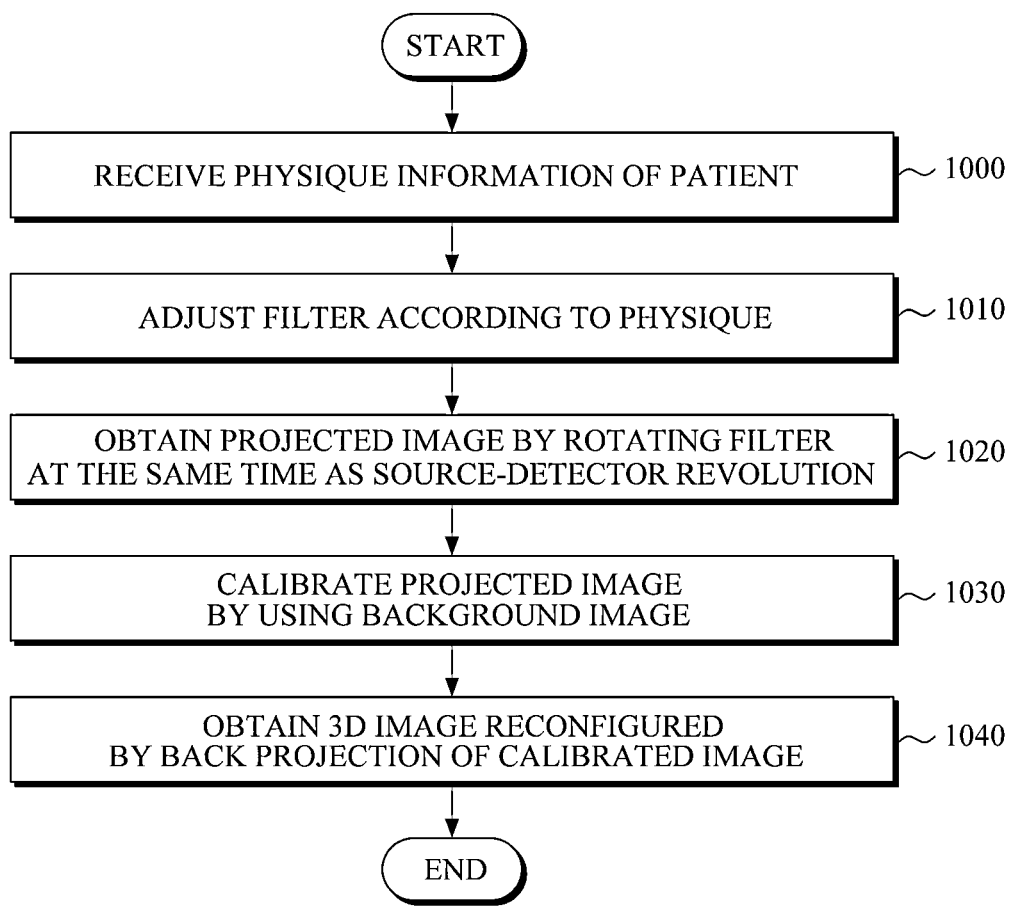
FIG. 10 is a flowchart illustrating an example method of CT imaging using a filter according to an exemplary embodiment.

FIG. 10 is a flowchart illustrating an example method of CT imaging using a filter according to an exemplary embodiment.

Referring to FIG. 10, physique information of a patient to be imaged by CT is first received in 1000, in either manner of manual input by a user, or automatic input by measuring physique information of a patient on a sensored couch where the patient lies.

Subsequently, according to the input physique information of a patient, an appropriate filter may be selected, or a filter may be moved to an appropriate position in 1010. Then, a filter is rotated at the same time as revolution of the source-detector to obtain projected images in 1020.

Thereafter, by using background projected images obtained in advance by rotating a filter at the same with the source-detector revolution without a human body, the projected images obtained in 1020 are calibrated for every pixel in 1030. For example, the calibration may generally be performed using $-\log[I(x)/I_0(x)]$, as an operation of quantifying X-ray attenuation, in which $I(x)$ represents x-th pixel value of a projected image, and $I_0(x)$ represents x-th pixel value of a background projected image.

Lastly, a complete 3D image reconstructed by back projection of the calibrated image is obtained in 1040. As the reconstructed image thus obtained may be significantly affected by a blurring effect, filtering may be performed to emphasize edges of the calibrated image before back projection, so as to obtain a clear, reconstructed-image.

According to an exemplary embodiment, by adaptively adjusting X-ray intensity distribution according to revolution angles, a dose of X-rays irradiating to a human body may be reduced, and images with an optimal quality may be obtained. For example, by adaptively adjusting X-ray intensity distribution to an environment where a thickness and width of a human body to be irradiated with X-rays are different according to revolution of an X-ray source, an X-ray dose may be reduced, and images with optimal quality may be obtained.

Further, based on physique information of a patient, a filter size may be selected, or a position or distance of the filter may be adjusted, thereby reducing an x-ray dose. For example, depending on different physiques of patients, filters of different sizes may be selected appropriately for imaging of each patient, or when using one filter, a distance between the filter and a subject may be adjusted for imaging, such that X-rays irradiating a thick body part are adjusted to be intense, and X-rays irradiating a thin body part are adjusted to be weak, thereby reducing an X-ray dose.

Moreover, according to an exemplary embodiment, a structure is simple, enabling easy production and installation. For example, an outer part of the filter is of a cylindrical shape, and an inner part thereof is of a cylindroid shape, or the outer part thereof is of a cylindroid shape, and the inner part thereof is of a cylindrical shape, thereby enabling easy production and installation.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims. Further, the above-described examples are for illustrative explanation of the present invention, and thus, the present invention is not limited thereto.

What is claimed is:

1. An X-ray distribution adjusting filter comprising an outer part integral with an inner part,
    wherein the inner part has a long axis and a short axis, and positions of the long axis and the short axis of the inner part are changed according to rotation angles of the X-ray distribution adjusting filter toward a subject, such that X-ray intensity distribution is adaptively adjusted to an environment where a thickness and a width of the subject are different, and
    wherein a controller is configured to use physique information of the subject to adjust a distance between a horizontal axis of the X-ray distribution adjusting filter and an X-ray source.

2. The X-ray distribution adjusting filter of claim 1, wherein the X-ray source and an X-ray detector are disposed to face each other with the subject interposed therebetween, and configured to revolve around the subject such that the X-ray distribution adjusting filter rotates with an angle identical to an angle of the revolution of the X-ray source and the X-ray detector, such that the positions of the long axis and the short axis of the inner part toward the subject are changed.

3. The X-ray distribution adjusting filter of claim 2, wherein the X-ray source revolves to be disposed at a position to radiate X-rays in a lateral direction of the subject such that the long axis of the inner part is directed toward the lateral direction of the subject, and the X-ray source revolves to be disposed at a position to radiate X-rays in an anteroposterior direction of the subject such that the short axis of the inner part is directed toward the anteroposterior direction of the subject.

4. The X-ray distribution adjusting filter of claim 1, wherein the outer part of the X-ray distribution adjusting filter has a cylindrical shape, and the inner part of the X-ray distribution adjusting filter has a cylindroid shape.

5. The X-ray distribution adjusting filter of claim 1, wherein both of the outer part and the inner part of the x-ray distribution adjusting filter have a cylindroid shape.

6. The X-ray distribution adjusting filter of claim 5, wherein each cylindroid of the outer part and the inner part has a different long axis/short axis ratio.

7. The X-ray distribution adjusting filter of claim 1, wherein the X-ray distribution adjusting filter has a frusto-conical shape.

8. The X-ray distribution adjusting filter of claim 1, wherein the X-ray distribution adjusting filter has an array structure with a plurality of filters of different sizes connected with each other or integrally formed.

9. A CT apparatus, comprising:
a gantry configured to comprise an X-ray source and an X-ray detector, which are disposed to face each other with a subject interposed therebetween, and to revolve around the subject to scan the subject;
an X-ray distribution adjusting filter, which is disposed between the X-ray source and the X-ray detector of the gantry, has an outer part integral with an inner part, and is configured to rotate according to revolution of the X-ray source and the X-ray detector such that a shape of the X-ray distribution adjusting filter is changed according to revolution angles to adjust intensity distribution of X-rays radiating toward the subject;
an actuator configured to rotate the X-ray distribution adjusting filter; and
a controller configured to use physique information of the subject to adjust a distance between a horizontal axis of the X-ray distribution adjusting filter and the X-ray source.

10. The CT apparatus of claim 9, wherein the X-ray source and the X-ray detector revolves around the subject such that the X-ray distribution adjusting filter rotates with an angle identical to an angle of the revolution of the X-ray source and the X-ray detector, and positions of a long axis and a short axis of an inner part of the X-ray distribution adjusting filter are changed, such that the X-ray distribution adjusting filter adaptively adjusts X-ray intensity distribution to an environment where a thickness and a width of the subject are different.

11. The CT apparatus of claim 10, wherein the actuator is configured to rotate the X-ray distribution adjusting filter so that the X-ray source revolves to be disposed at a position to radiate X-rays in a lateral direction of the subject such that the long axis of the inner part of the X-ray distribution adjusting filter is directed toward the lateral direction of the subject, and the X-ray source revolves to be disposed at a position to radiate X-rays in an anteroposterior direction of the subject such that the short axis of the inner part of the X-ray distribution adjusting filter is directed toward the anteroposterior direction of the subject.

12. The CT apparatus of claim 9, wherein the outer part of the X-ray distribution adjusting filter has a cylindrical shape, and the inner part of the X-ray distribution adjusting filter has a cylindroid shape.

13. The CT apparatus of claim 9, wherein both of the outer part and the inner part of the X-ray distribution adjusting filter have a cylindroid shape.

14. The CT apparatus of claim 9, wherein the controller is configured to use the physique information of the subject to select a filter corresponding to the subject's physique.

15. The CT apparatus of claim 14, wherein the controller is configured to adjust, according to the X-ray source, the distance between the X-ray distribution adjusting filter and the X-ray source through the actuator according to physique or body tissues of the subject.

16. The CT apparatus of claim 14, wherein:
the X-ray distribution adjusting filter has a frusto-conical shape; and
the controller is configured to move the X-ray distribution adjusting filter of a frusto-conical shape in a horizontal direction of an axis of the X-ray distribution adjusting filter of a frusto-conical shape through the actuator according to physique or body tissues of the subject.

17. A CT method, comprising:
along with revolution of an X-ray source and an X-ray detector, which are disposed to face each other in a gantry with a subject interposed therebetween, rotating an X-ray distribution adjusting filter, which has an outer part integral with an inner part and is disposed between the X-ray source and the X-ray detector;
receiving physique information of a subject to be imaged by CT;
adjusting, according to the X-ray source, a distance between a horizontal axis of the X-ray distribution adjusting filter and the X-ray source according to the received physique information of the subject;
adjusting intensity distribution of X-rays radiating toward a subject by the X-ray distribution adjusting filter;
obtaining projected data from the subject according to the adjustment of X-ray intensity distribution; and
reconstructing the obtained projected data to obtain images.

18. The CT method of claim 17, wherein the adjusting of intensity distribution of X-rays comprises:
revolving the X-ray source to be disposed at a position to radiate X-rays in a lateral direction of the subject, and controlling the actuator to rotate the X-ray distribution adjusting so that a long axis of the inner part of the X-ray distribution adjusting filter is directed toward the lateral direction of the subject; and
revolving the X-ray source to be disposed at a position to radiate X-rays in an anteroposterior direction of the subject, and controlling the actuator to rotate the X-ray distribution adjusting filter so that a short axis of the inner part of the X-ray distribution adjusting filter is directed toward the anteroposterior direction of the subject.

19. The CT method of claim 17, further comprising:
selecting an X-ray distribution adjusting filter suitable for the received physique information of the subject among X-ray distribution adjusting filters of different sizes.

* * * * *